US012674188B2

(12) United States Patent
Lebeer et al.

(10) Patent No.: US 12,674,188 B2
(45) Date of Patent: Jul. 7, 2026

(54) LIMOSILACTOBACILLUS REUTERI STRAIN WITH HIGH RIBOFLAVIN PRODUCTION AND USES THEREOF

(71) Applicant: Universiteit Antwerpen, Antwerp (BE)

(72) Inventors: Sarah Lebeer, Antwerp (BE); Sarah Ahannach, Antwerp (BE); Irina Spacova, Antwerp (BE); Stijn Wittouck, Antwerp (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 414 days.

(21) Appl. No.: 18/254,531

(22) PCT Filed: Nov. 30, 2021

(86) PCT No.: PCT/EP2021/083615
§ 371 (c)(1),
(2) Date: May 25, 2023

(87) PCT Pub. No.: WO2022/112609
PCT Pub. Date: Jun. 2, 2022

(65) Prior Publication Data
US 2024/0011067 A1       Jan. 11, 2024

(30) Foreign Application Priority Data
Nov. 30, 2020    (EP) .................................... 20210606

(51) Int. Cl.
| | |
|---|---|
| *A61K 35/74* | (2015.01) |
| *C12N 1/205* | (2026.01) |
| *C12N 9/04* | (2006.01) |
| *C12N 9/10* | (2006.01) |
| *C12N 9/12* | (2006.01) |
| *C12N 9/78* | (2006.01) |
| *C12N 9/88* | (2006.01) |
| *C12P 25/00* | (2006.01) |
| *C12R 1/225* | (2006.01) |

(52) U.S. Cl.
CPC ............ *C12P 25/00* (2013.01); *C12N 9/0006* (2013.01); *C12N 9/1085* (2013.01); *C12N 9/1205* (2013.01); *C12N 9/1241* (2013.01); *C12N 9/78* (2013.01); *C12N 9/88* (2013.01); *C12Y 101/01193* (2013.01); *C12Y 205/01009* (2013.01); *C12Y 205/01078* (2013.01); *C12Y 207/01026* (2013.01); *C12Y 207/07002* (2013.01); *C12Y 305/04026* (2013.01); *C12Y 401/99012* (2013.01)

(58) Field of Classification Search
CPC ............. C12P 25/00; C12Y 205/01009; C12Y 207/01026; C12Y 207/07002; C12Y 305/04025; C12R 2001/225; C12R 2001/01; C12N 1/205; C12N 1/20; A61K 35/74
See application file for complete search history.

(56) References Cited

PUBLICATIONS

International Search Report and Written Opinion mailed Mar. 11, 2022 in reference to co-pending European Application PCT/EP2021/083615 filed Nov. 30, 2021.
Dey, S., Bishayi, B. (2016). Riboflavin along with antibiotics balances reactive oxygen species and inflammatory cytokines and controls Staphylococcus aureus infection by boosting murine macrophage function and regulates inflammation. J Inflamm (Lond). 13:36. doi:10.1186/s12950-016-0145-0.
Jayashree, S., Jayaraman, K., and Kalaichelvan, G. (2010) Isolation, screening and characterization of riboflavin producing lactic acid bacteria from Katpadi, Vellore district. Recent Res Sci Technol 2: 83-88.
Juarez del Valle, M., Laiño, J. E., Savoy de Giori, G., & LeBlanc, J. G. (2017). Factors stimulating riboflavin produced by Lactobacillus plantarum CRL 725 grown in a semi-defined medium. Journal of Basic Microbiology, 57(3), 245-252.
Lim, S. H., Choi, J. S., & Park, E. Y. (2001). Microbial production of riboflavin using riboflavin overproducers, Ashbya gossypii, Bacillus subtilis, and Candida famate: An overview. Biotechnology and Bioprocess Engineering, 6(2), 75-88.
Mortelé, O., Iturrospe, E., Breynaert, A., Verdickt, E., Xavier, B. B., Lammens, C., Malhotra-Kumar, S., Jorens, P. G., Pieters, L., van Nuijs, A., & Hermans, N. (2019). Optimization of an in vitro gut microbiome biotransformation platform with chlorogenic acid as model compound: From fecal sample to biotransformation product identification. Journal of pharmaceutical and biomedical analysis, 175, 112768. https://doi.org/10.1016/j.jpba.2019.07.016.
Stahmann, K. P., Revuelta, J. L., & Seulberger, H. (2000). Three biotechnical processes using Ashbya gossypii, Candida famata, or Bacillus subtilis compete with chemical riboflavin production. Applied Microbiology and Biotechnology, 53(5), 509-516.
(Continued)

*Primary Examiner* — Satyendra K Singh
(74) *Attorney, Agent, or Firm* — DINSMORE & SHOHL LLP

(57) ABSTRACT

The present invention to the identification of a novel isolated bacterial strain, the *Limosilactobacillus reuteri* strain which is characterized by a naturally occurring overproduction of riboflavin (vitamin B2) compared to other known strains of lactobacilli. Said strain of the *Limosilactobacillus* species is deposited under accession number LMG P-32020. In a further aspect, also the uses of said *L. reuteri* strain are disclosed herein. In particular, the use of said strain in food and feed industry, human and veterinary health, large-scale vitamin production, cosmetics and consumer care products is disclosed.

16 Claims, 6 Drawing Sheets

Specification includes a Sequence Listing.

(56) References Cited

PUBLICATIONS

Thakur, K., Tomar, S. K., & De, S. (2016). Lactic acid bacteria as a cell factory for riboflavin production. Microbial Biotechnology, 9(4), 441-451.

Thakur, K., and Tomar, S.K. (2015) Exploring indigenous *Lactobacillus* species from diverse niches for riboflavin production. J Young Pharmacists 7: 122-127.

Morita Hidetoshi et al: "Comparative genome analysis of Lactobacillus reuteri and Lactobacillus fermentum reveal a genomic island for reuterin and cobalamin production", DNA Research, Universal Academy Press, JP, vol. 15, No. 3, Jun. 30, 2008 (Jun. 30, 2008), pp. 151-161, XP002509881.

Fig. 1

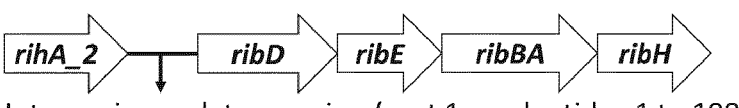

Intergenic regulatory region (part 1: nucleotides 1 to 198)

```
                              10         20         30
DSM20016    1 - - A A T T T G C T G T T T A C A A A A A G A A A G T G A A G A G T  32
AMBV339_    1 C T A A T T T A T T G T T T A C A A A A A T A A T G T G A A G A G T  34
AMBV371_    1 C T A A T T T A T T G T T T A C A A A A A T A A T G T G A A G A G T  34
AMBV369_    1 C T A A T T T A T T G T T T A C A A A A A T A A T G T G A A G A G T  34
AMBV368_    1 C T A A T T T A T T G T T T A C A A A A A T A A T G T G A A G A G T  34
AMBV337_    1 C T A A T T T A T T G T T T A C A A A A A T A A T G T G A A G A G T  34
AMBV336_    1 C T A A T T T A T T G T T T A C A A A A A T A A T G T G A A G A G T  34

40         50         60
DSM20016   33 T A C A C T A T A T G T A A A T T T A A C A A T C T - A A T T T T C  65
AMBV339_   35 T A A A C T A T G T G T A A A C T T A A C A A T C T A A A T T T T C  68
AMBV371_   35 T A A A C T A T G T G T A A A C T T A A C A A T C T A A A T T T T C  68
AMBV369_   35 T A A A C T A T G T G T A A A C T T A A C A A T C T A A A T T T T C  68
AMBV368_   35 T A A A C T A T G T G T A A A C T T A A C A A T C T A A A T T T T C  68
AMBV337_   35 T A A A C T A T G T G T A A A C T T A A C A A T C T A A A T T T T C  68
AMBV336_   35 T A A A C T A T G T G T A A A C T T A A C A A T C T A A A T T T T C  68

70         80         90        100
DSM20016   66 T T C G G G G C A G G G T G A A A T T C C C A A C C G A C G G T A A  99
AMBV339_   69 T T C G G G G C A G T G T G A A A T T C C C A A C C G A C G G T A A 102
AMBV371_   69 T T C G G G G C A G G G T G A A A T T C C C A A C C G A C G G T A A 102
AMBV369_   69 T T C G G G G C A G G G T G A A A T T C C C A A C C G A C G G T A A 102
AMBV368_   69 T T C G G G G C A G G G T G A A A T T C C C A A C C G A C G G T A A 102
AMBV337_   69 T T C G G G G C A G G G T G A A A T T C C C A A C C G A C G G T A A 102
AMBV336_   69 T T C G G G G C A G G G T G A A A T T C C C A A C C G A C G G T A A 102

110        120        130
DSM20016  100 C A A G T A C G C T T G G A G T C C G T G A C C C G T T A G C A T T 133
AMBV339_  103 C A A G T A C G C T T G G A G T C C G T G A C C C G T T A G C A T T 136
AMBV371_  103 C A A G T A C G C T T G G A G T C C G T G A C C C G T T A G C A T T 136
AMBV369_  103 C A A G T A C G C T T G G A G T C C G T G A C C C G T T A G C A T T 136
AMBV368_  103 C A A G T A C G C T T G G A G T C C G T G A C C C G T T A G C A T T 136
AMBV337_  103 C A A G T A C G C T T G G A G T C C G T G A C C C G T T A G C A T T 136
AMBV336_  103 C A A G T A C G C T T G G A G T C C G T G A C C C G T T A G C A T T 136

140        150        160
DSM20016  134 T A T G T T A A C G G T T G A A C C A G T G A A A A T C T G G T A C 167
AMBV339_  137 T A T G T T A A C G G T T G A A C C A G T G A A A A T C T G G T A C 170
AMBV371_  137 T A T G T T A A C G G T T G A A C C A G T G A A A A T C T G G T A C 170
AMBV369_  137 T A T G T T A A C G G T T G A A C C A G T G A A A A T C T G G T A C 170
AMBV368_  137 T A T G T T A A C G G T T G A A C C A G T G A A A A T C T G G T A C 170
AMBV337_  137 T A T G T T A A C G G T T G A A C C A G T G A A A A T C T G G T A C 170
AMBV336_  137 T A T G T T A A C G G T T G A A C C A G T G A A A A T C T G G T A C 170
```

Fig. 1 – Continued

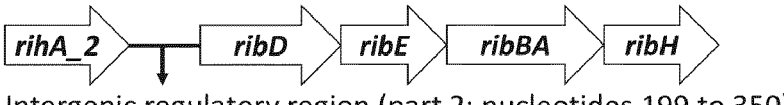

Intergenic regulatory region (part 2; nucleotides 199 to 350)

```
                               180        190        200
DSM20016 168 CGACAGTATAGTCTGGATGGGAGAAGAAAACTAA 201
AMBV339_ 171 CGACAGTATAGTCTGGATGGGAGAAGAAAACTAA 204
AMBV371_ 171 CGACAGTATAGTCTGGATGGGAGAAGAAAACTAA 204
AMBV369_ 171 CGACAGTATAGTCTGGATGGGAGAAGAAAACTAA 204
AMBV368_ 171 CGACAGTATAGTCTGGATGGGAGAAGAAAACTAA 204
AMBV337_ 171 CGACAGTATAGTCTGGATGGGAGAAGAAAACTAA 204
AMBV336_ 171 CGACAGTATAGTCTGGATGGGAGAAGAAAACTAA 204

210        220        230
DSM20016 202 AAATGACACAATCAGTTTAAACGTAAAGCCCCGG 235
AMBV339_ 205 AAATGACACAATCAGTTTAAACGTAAAGCCCCGG 238
AMBV371_ 205 AAATGACACAATCAGTTTAAACGTAAAGCCCCGG 238
AMBV369_ 205 AAATGACACAATCAGTTTAAACGTAAAGCCCCGG 238
AMBV368_ 205 AAATGACACAATCAGTTTAAACGTAAAGCCCCGG 238
AMBV337_ 205 AAATGACACAATCAGTTTAAACGTAAAGCCCCGG 238
AMBV336_ 205 AAATGACACAATCAGTTTAAACGTAAAGCCCCGG 238

240        250        260        270
DSM20016 236 ATAGCAGTGATGTTATCCGGTTTTATTTTTGCCG 269
AMBV339_ 239 ATAGCAGTGATGTTATCCGGTTTTA-TTTTGCCG 271
AMBV371_ 239 ATAGCAGTGATGTTATCCGGTTTTA-TTTTGCCG 271
AMBV369_ 239 ATAGCAGTGATGTTATCCGGTTTTA-TTTTGCCG 271
AMBV368_ 239 ATAGCAGTGATGTTATCCGGTTTTA-TTTTGCCG 271
AMBV337_ 239 ATAGCAGTGATGTTATCCGGTTTTA-TTTTGCCG 271
AMBV336_ 239 ATAGCAGTGATGTTATCCGGTTTTA-TTTTGCCG 271

280        290        300
DSM20016 270 AGCTGTTTTTTTAAGTTAACTATTTAACGTCCCG 303
AMBV339_ 272 AGCTGTTTTTT--AGGTAACCATTTAACGCCCCG 303
AMBV371_ 272 AGCTGTTTTTT--AGGTAACCATTTAACGCCCCG 303
AMBV369_ 272 AGCTGTTTTTT--AGGTAACCATTTAACGCCCCG 303
AMBV368_ 272 AGCTGTTTTTT--AGGTAACCATTTAACGCCCCG 303
AMBV337_ 272 AGCTGTTTTTT--AGGTAACCATTTAACGCCCCG 303
AMBV336_ 272 AGCTGTTTTTT--AGGTAACCATTTAACGCCCCG 303

310        320        330
DSM20016 304 AGAG-AAATCTTAGGACGTTTTTATTTTGGAAAG 336
AMBV339_ 304 AGAGAAAATCTTAGGGCGTTTTTATTTTGGAAAG 337
AMBV371_ 304 AGAGAAAATCTTAGGGCGTTTTTATTTTGGAAAG 337
AMBV369_ 304 AGAGAAAATCTTAGGGCGTTTTTATTTTGGAAAG 337
AMBV368_ 304 AGAGAAAATCTTAGGGCGTTTTTATTTTGGAAAG 337
AMBV337_ 304 AGAGAAAATCTTAGGGCGTTTTTATTTTGGAAAG 337
AMBV336_ 304 AGAGAAAATCTTAGGGCGTTTTTATTTTGGAAAG 337

DSM20016_NC_009513.1_931749_932097
AMBV339_contig00004_68789_69138
AMBV371_contig00004_7606_7257
AMBV369_contig00005_7606_7257
AMBV368_contig00005_7606_7257
AMBV337_contig00004_7606_7257
AMBV336_contig00004_7606_7257
```

Fig. 2
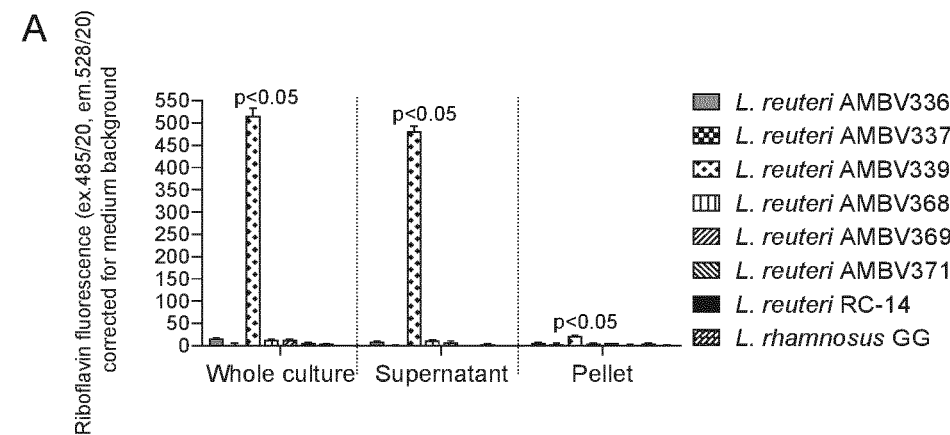
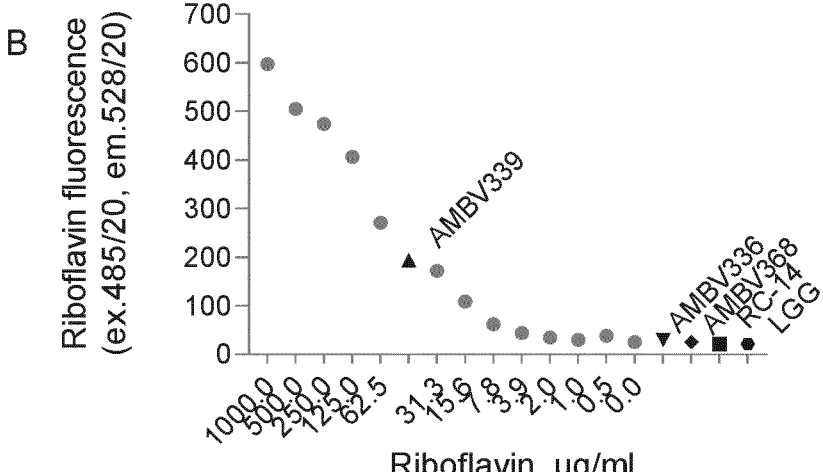
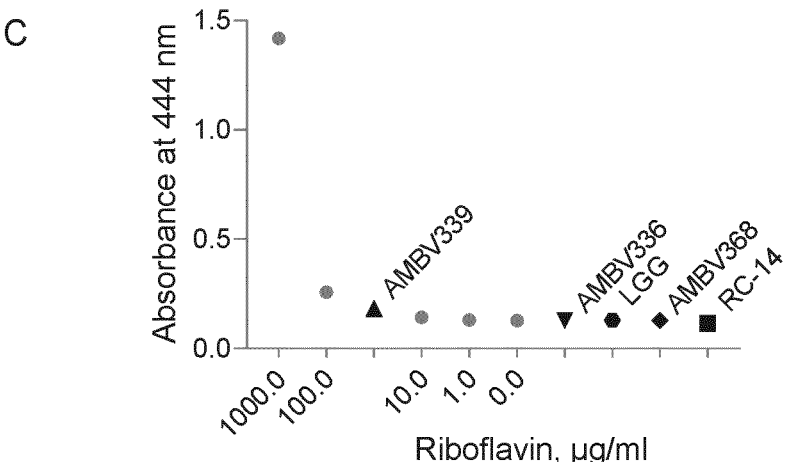

Fig. 3
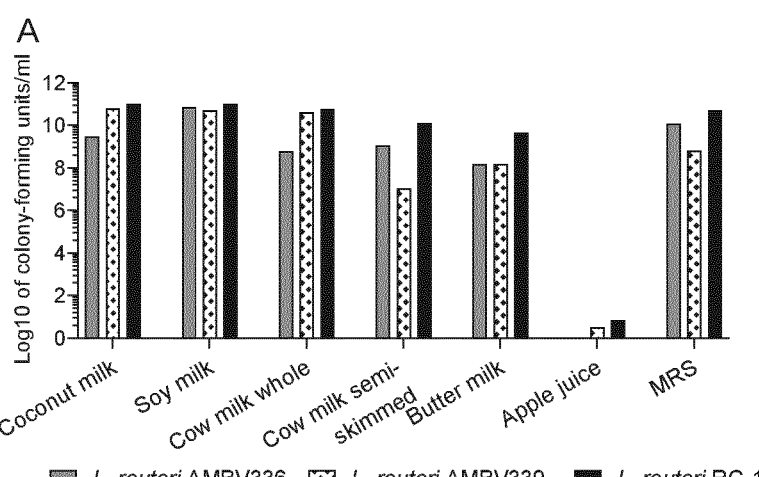
A
L. reuteri AMBV336　　L. reuteri AMBV339　　L. reuteri RC-14
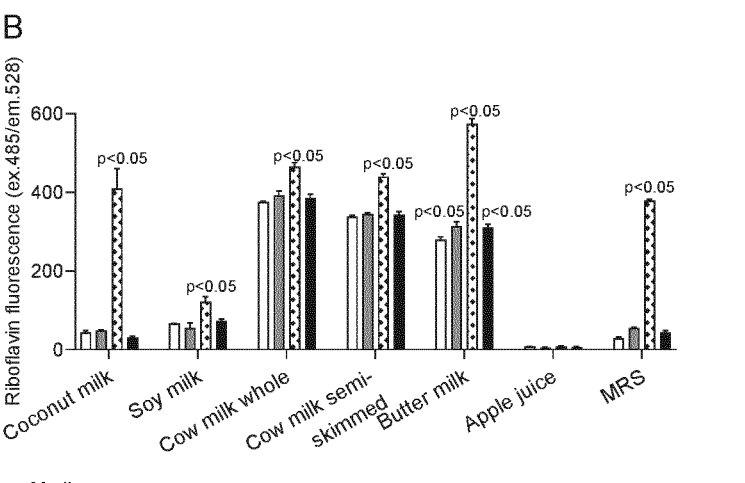
B
Medium　　L. reuteri AMBV336　　L. reuteri AMBV339　　L. reuteri RC-14
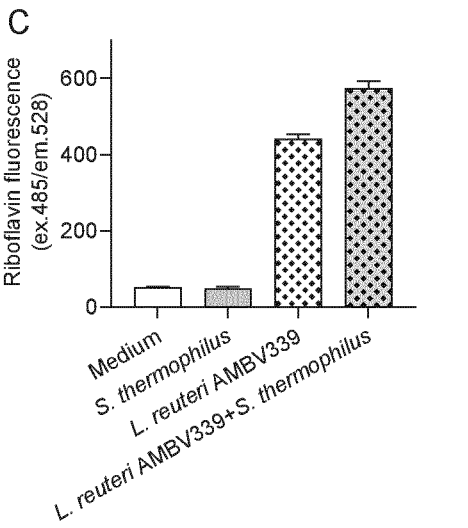
C

Fig. 4
A
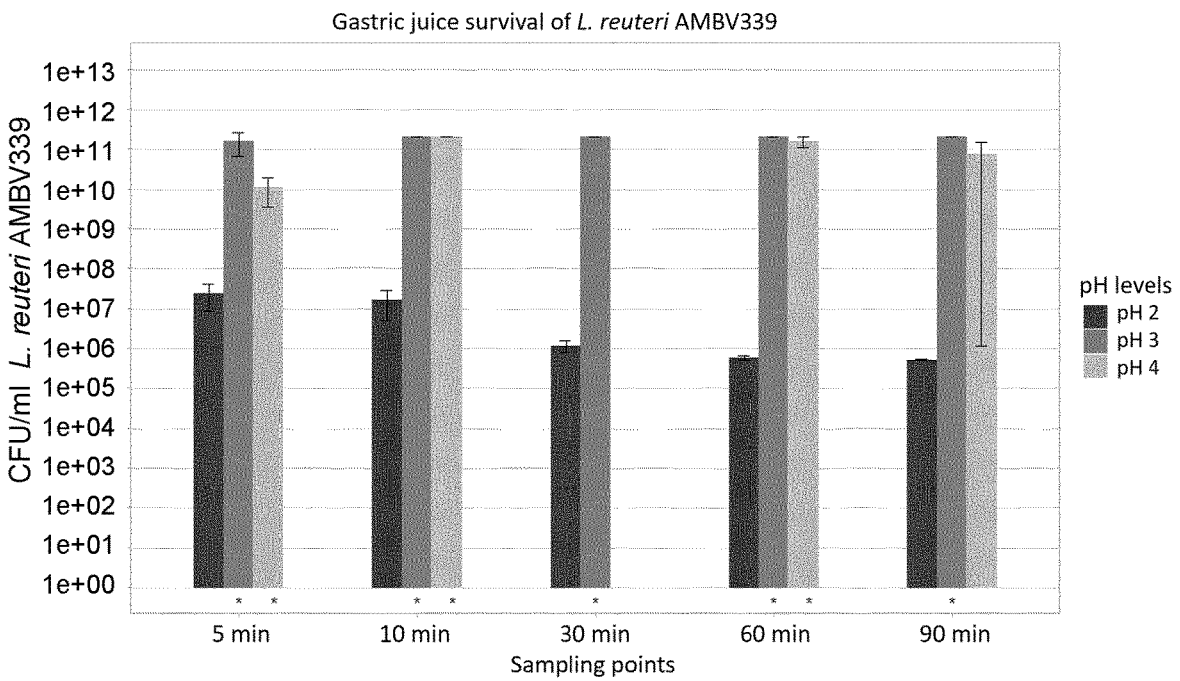
B
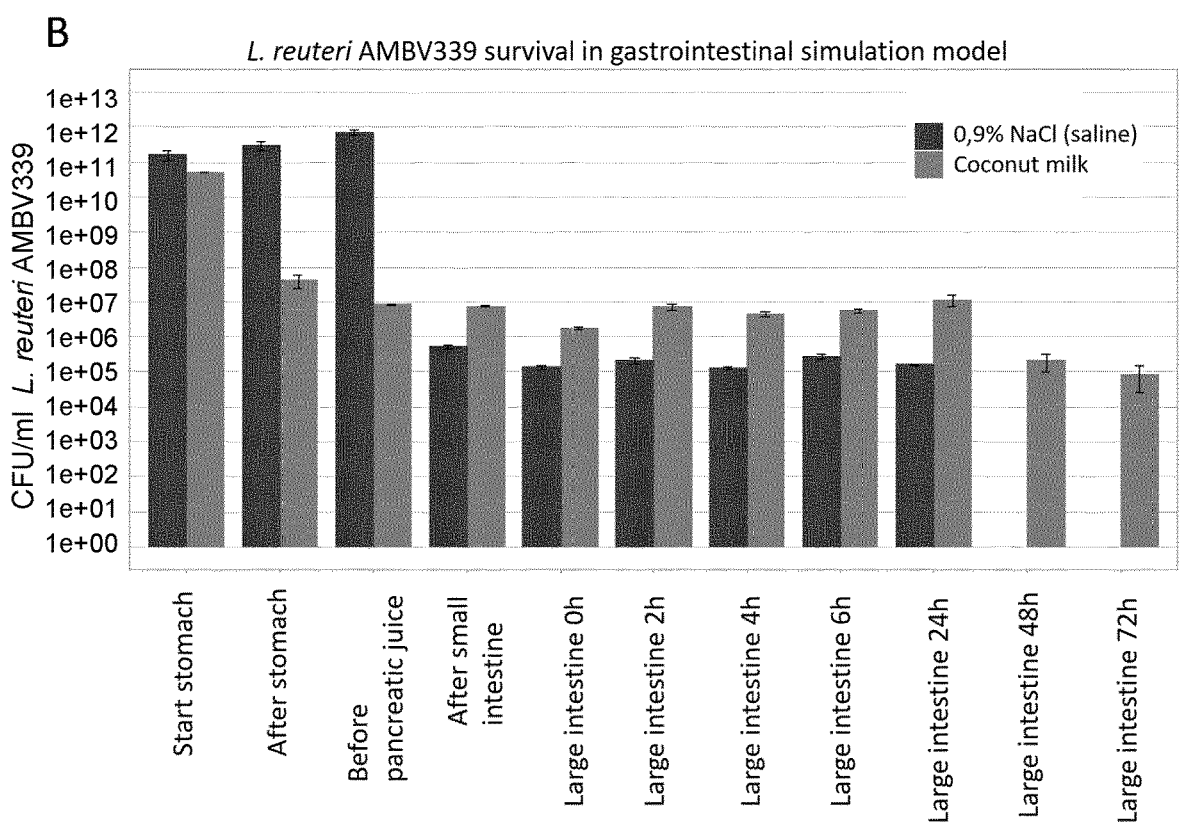

C

SEQUENCE LISTING

<160> NUMBER OF SEQ ID NOS: 7

<210> SEQ ID NO 1
<211> LENGTH: 350
<212> TYPE: DNA
<213> ORGANISM: Lactobacillus
<220> FEATURE:
<223> OTHER INFORMATION: AMBV339 - Intergenic Regulatory Region

<400> SEQUENCE: 1
ctaatttatt gtttacaaaa ataatgtgaa gagttaaact atgtgtaaac ttaacaatct      60

```
aaattttctt cggggcagtg tgaaattccc aaccgacggt aacaagtacg cttggagtcc      120
gtgacccgtt agcatttatg ttaacggttg aaccagtgaa aatctggtac cgacagtata      180
gtctggatgg gagaagaaaa ctaaaaatga cacaatcagt ttaaacgtaa agccccggat      240
agcagtgatg ttatccggtt ttattttgcc gagctgtttt ttaggtaacc atttaacgcc      300
ccgagagaaa atcttagggc gttttttattt tggaaaggat ggttagagtg               350
```

```
<210> SEQ ID NO 2
<211> LENGTH: 350
<212> TYPE: DNA
<213> ORGANISM: Lactobacillus
<220> FEATURE:
<223> OTHER INFORMATION: AMBV371 - Intergenic Regulatory Region

<400> SEQUENCE: 2
ctaatttatt gtttacaaaa ataatgtgaa gagttaaact atgtgtaaac ttaacaatct       60
aaattttctt cggggcaggg tgaaattccc aaccgacggt aacaagtacg cttggagtcc      120
gtgacccgtt agcatttatg ttaacggttg aaccagtgaa aatctggtac cgacagtata      180
gtctggatgg gagaagaaaa ctaaaaatga cacaatcagt ttaaacgtaa agccccggat      240
agcagtgatg ttatccggtt ttattttgcc gagctgtttt ttaggtaacc atttaacgcc      300
ccgagagaaa atcttagggc gttttttattt tggaaaggat ggttagagtg               350
```

```
<210> SEQ ID NO 3
<211> LENGTH: 350
<212> TYPE: DNA
<213> ORGANISM: Lactobacillus
<220> FEATURE:
<223> OTHER INFORMATION: AMBV369 - Intergenic Regulatory Region

<400> SEQUENCE: 3
ctaatttatt gtttacaaaa ataatgtgaa gagttaaact atgtgtaaac ttaacaatct       60
aaattttctt cggggcaggg tgaaattccc aaccgacggt aacaagtacg cttggagtcc      120
gtgacccgtt agcatttatg ttaacggttg aaccagtgaa aatctggtac cgacagtata      180
gtctggatgg gagaagaaaa ctaaaaatga cacaatcagt ttaaacgtaa agccccggat      240
agcagtgatg ttatccggtt ttattttgcc gagctgtttt ttaggtaacc atttaacgcc      300
ccgagagaaa atcttagggc gttttttattt tggaaaggat ggttagagtg               350
```

```
<210> SEQ ID NO 4
<211> LENGTH: 350
<212> TYPE: DNA
<213> ORGANISM: Lactobacillus
<220> FEATURE:
<223> OTHER INFORMATION: AMBV368 - Intergenic Regulatory Region

<400> SEQUENCE: 4
ctaatttatt gtttacaaaa ataatgtgaa gagttaaact atgtgtaaac ttaacaatct       60
aaattttctt cggggcaggg tgaaattccc aaccgacggt aacaagtacg cttggagtcc      120
gtgacccgtt agcatttatg ttaacggttg aaccagtgaa aatctggtac cgacagtata      180
gtctggatgg gagaagaaaa ctaaaaatga cacaatcagt ttaaacgtaa agccccggat      240
agcagtgatg ttatccggtt ttattttgcc gagctgtttt ttaggtaacc atttaacgcc      300
ccgagagaaa atcttagggc gttttttattt tggaaaggat ggttagagtg               350
```

```
<210> SEQ ID NO 5
<211> LENGTH: 350
```

-continued

```
<212> TYPE: DNA
<213> ORGANISM: Lactobacillus
<220> FEATURE:
<223> OTHER INFORMATION: AMBV337 - Intergenic Regulatory Region

<400> SEQUENCE: 5
ctaatttatt gtttacaaaa ataatgtgaa gagttaaact atgtgtaaac ttaacaatct      60
aaattttctt cggggcaggg tgaaattccc aaccgacggt aacaagtacg cttggagtcc     120
gtgacccgtt agcatttatg ttaacggttg aaccagtgaa aatctggtac cgacagtata     180
gtctggatgg gagaagaaaa ctaaaaatga cacaatcagt ttaaacgtaa agccccggat     240
agcagtgatg ttatccggtt ttattttgcc gagctgtttt ttaggtaacc atttaacgcc     300
ccgagagaaa atcttagggc gtttttattt tggaaaggat ggttagagtg               350

<210> SEQ ID NO 6
<211> LENGTH: 350
<212> TYPE: DNA
<213> ORGANISM: Lactobacillus
<220> FEATURE:
<223> OTHER INFORMATION: AMBV336 - Intergenic Regulatory Region

<400> SEQUENCE: 6
ctaatttatt gtttacaaaa ataatgtgaa gagttaaact atgtgtaaac ttaacaatct      60
aaattttctt cggggcaggg tgaaattccc aaccgacggt aacaagtacg cttggagtcc     120
gtgacccgtt agcatttatg ttaacggttg aaccagtgaa aatctggtac cgacagtata     180
gtctggatgg gagaagaaaa ctaaaaatga cacaatcagt ttaaacgtaa agccccggat     240
agcagtgatg ttatccggtt ttattttgcc gagctgtttt ttaggtaacc atttaacgcc     300
ccgagagaaa atcttagggc gtttttattt tggaaaggat ggttagagtg               350

<210> SEQ ID NO 7
<211> LENGTH: 349
<212> TYPE: DNA
<213> ORGANISM: Lactobacillus
<220> FEATURE:
<223> OTHER INFORMATION: DSM20016 - Intergenic Regulatory Region

<400> SEQUENCE: 7
aatttgctgt ttacaaaaag aaagtgaaga gttacactat atgtaaattt aacaatctaa      60
ttttcttcgg ggcagggtga aattcccaac cgacggtaac aagtacgctt ggagtccgtg     120
acccgttagc atttatgtta acggttgaac cagtgaaaat ctggtaccga cagtatagtc     180
tggatgggag aagaaaacta aaaatgacac aatcagttta aacgtaaagc cccggatagc     240
agtgatgtta tccggtttta ttttgccga gctgtttttt taagttaact atttaacgtc     300
ccgagagaaa tcttaggacg tttttatttt ggaaaggatg gttagagtg                349
```

LIMOSILACTOBACILLUS REUTERI STRAIN WITH HIGH RIBOFLAVIN PRODUCTION AND USES THEREOF

CROSS REFERENCES TO RELATED APPLICATIONS

This application is a national-stage application under 35 U.S.C. § 371 of International Application PCT/EP2021/083615, filed Nov. 30, 2021, which International Application claims benefit of priority to European Patent Application No. 20210606.8, filed Nov. 30, 2020.

FIELD OF THE INVENTION

The present invention to the identification of a novel isolated bacterial strain, the *Limosilactobacillus reuteri* strain which is characterized by a naturally occurring over-production of riboflavin (vitamin B2) compared to other known strains of lactobacilli. Said strain of the *Limosilactobacillus* species is deposited under accession number LMG P-32020. In a further aspect, also the uses of said *L. reuteri* strain are disclosed herein. In particular, the use of said strain in food and feed industry, human and veterinary health, large-scale vitamin production, cosmetics and consumer care products is disclosed.

BACKGROUND TO THE INVENTION

Riboflavin (vitamin B2) is an essential water-soluble yellow-green fluorescent vitamin that participates in macronutrient and energy metabolism (fats, proteins and carbohydrates), has antioxidant functions and activates other vitamins such as folate and pyridoxine. Riboflavin is required by all life forms, and in humans it is important for reproductive function, lactation, successful pregnancy outcomes, development of children and adequate energy levels. The current average requirements are 0.5-1.4 mg riboflavin/day for children and 1.3 mg/day for adults as defined by the European Food Safety Authority (EFSA, 2017, EFSA-Q-2011-01222). According to Oregon State University, during pregnancy, women should have 1.4 milligrams per day, and when breastfeeding, 1.6 milligrams per day. Furthermore, riboflavin deficiency can lead to skin damage, sore throat, oedema of oral and mucous membranes, cheilosis and glossitis. Riboflavin intake can reverse these symptoms, and further improve efficiency of standard therapies against common viral and bacterial infectious diseases (Dey and Bishayi, 2016), such as *Staphylococcus aureus* infection. Based on the scientific opinion of the EFSA Panel on Dietetic Products, Nutrition and Allergies (NDA) (2010), authorised health claims in the EU Register for foods which are a source of riboflavin include contribution to normal energy-yielding metabolism, maintenance of the normal function of the nervous system, maintenance of normal skin and mucous membranes, maintenance of normal red blood cells, maintenance of normal vision, contribution to normal metabolism of iron, protection of DNA, proteins and lipids from oxidative damage, reduction of tiredness and fatigue (Commission Regulation (EU) 432/2012 of 16 May 2012). Riboflavin is also used in animal feed to improve animal health, and it is used as food colouring with the food additive E number E101 in Europe.

In large-scale industrial settings, riboflavin was traditionally produced by chemical synthesis. However, in the last decades microbial synthesis of riboflavin is increasingly implemented because of economic and environmental considerations. Riboflavin can be obtained from natural over-producer microorganisms, mostly filamentous fungi and yeasts (*Eremothecium ashbyii, Ashbya gossypii* and *Candida famata*) and *Bacillus subtilis* mutants (Lim et al., 2001; Stahmann et al., 2000). While lactic acid bacteria have previously also been shown to produce riboflavin (Thakur et al, 2016), the lactic acid bacterial strains reported so far produce only limited amount of riboflavin, for example in a range of maximum 2.3-3 µg/ml of culture medium (Thakur and Tomar, 2015; Jayashree et al., 2010). Methods have been described to stimulate increased riboflavin production in lactobacilli. However, this requires defined conditions and still have only led to riboflavin concentrations of 5-6 µg/mL medium (Juarez del Valle et al., 2017). While recombinant *Lactococcus lactis* NZ9000 genetically modified for over-expression of ribG, ribB, ribA and ribH genes, was shown to produce as much as 24 µg riboflavin/ml medium, the use of genetically modified lactobacilli is currently not permitted in food products for human consumption for regulatory reasons. Riboflavin concentrations are typically around 26-30 mg/mL in industrial processes with e.g. *Eremothecium ashbyii*. Nevertheless an important consideration is that these concentrations are obtained with filamentous fungi and yeasts and not with lactobacilli that have a favourable safety profile in humans. Lactic acid bacteria are already widely implemented in the food industry or as probiotic formulations (e.g. *Limosilactobacillus reuteri* RC-14 and *Lacticaseibacillus rhamnosus* GG). Therefore, lactobacilli capable of enhanced vitamin production are of great interest for vitamin enrichment of food, feed and various probiotic formulations, supplements and even medicines. The riboflavin concentrations naturally occurring in previously described lactobacilli would not meet the needs of industrial production or food fermentation on a large scale, considering the current average requirements for children and adults.

Lactobacilli naturally overproducing riboflavin can thus prevent or treat riboflavin deficiency in humans and animals by providing a cost-effective and safe food fortification solution, or a probiotic or postbiotic product. Their administration to humans and animals can improve systemic and/or mucosal immune health, resistance to pathogens, macronutrient/energy metabolism and antioxidant function, and reproductive and offspring health.

SUMMARY OF THE INVENTION

The present invention is based on the identification of novel *Limosilactobacillus* strains that show an increased production of riboflavin. In particular the inventors found that said *Limosilactobacillus* strains have alterations in genes that are associated with the riboflavin pathway. More specifically, the present invention is based on the identification of a novel isolated strain of the *Limosilactobacillus reuteri* (*L. reuteri*) species. Said strain has been deposited with the Belgian Co-ordinated Collection of Micro-Organisms (BCCM), Universiteit Gent, K. L. Ledeganckstraat 35, 9000 Gent, Belgium) on Oct. 9, 2020 with accession number LMG P-32020, and herein further also indicated as *L. reuteri* AMBV339 or AMBV339 strain.

Typical for this novel isolated strain of the *L. reuteri* species is that it has a naturally occurring overproduction of riboflavin, also known as vitamin B2. In particular, the AMBV339 strain is capable of producing high levels of riboflavin, in particular as compared to other known strains of lactobacilli.

Therefore, in a first aspect, the present application is thus directed to one or more isolated *Limosilactobacillus* bacterial strains that have a naturally occurring overproduction of riboflavin. In particular, the present application discloses one or more isolated *Limosilactobacillus* bacterial strains that have alterations in one or more genes or regulatory genetic sequences that are associated with the riboflavin production pathway. In a particular embodiment, said strain of the present invention has an alternation in one or more genes or upstream regulatory sequences thereof compared to said genes or regulatory sequences of the *Limosilactobacillus reuteri* type strain DSM20016. In another particular embodiment, said genes are selected from the genes for 3,4-dihydroxy-2-butanone 4-phosphate synthase (EC 4.1.99.12) and/or GTP cyclohydrolase II (EC 3.5.4.25), Diaminohydroxyphosphoribosylaminopyrimidine deaminase (EC 3.5.4.26) and/or 5-amino-6-(5-phosphoribosylamino)uracil reductase (EC 1.1.1.193), 6,7-dimethyl-8-ribityllumazine synthase (EC 2.5.1.78), Riboflavin synthase eubacterial/eukaryotic (EC 2.5.1.9), FMN adenylyltransferase (EC 2.7.7.2) and/or Riboflavin kinase (EC 2.7.1.26), RibT protein, riboflavin biosynthesis acetyltransferase (GNAT) family, or substrate-specific component RibU of riboflavin ECF transporter.

In particular, such regulatory genetic sequences are selected from the promoters, riboswitches or other regulatory sequences upstream of said genes or genetic operons they belong to. In a specific embodiment, the present application discloses one or more isolated *Limosilactobacillus* bacterial strains that have alterations in the regulatory region upstream of genes or genetic operon involved in riboflavin production, in particular the genes for Diaminohydroxyphosphoribosylaminopyrimidine deaminase (EC 3.5.4.26) and/or 5-amino-6-(5-phosphoribosylamino)uracil reductase (EC 1.1.1.193) also known as ribD, Riboflavin synthase eubacterial/eukaryotic (EC 2.5.1.9) also known as ribE, 3,4-dihydroxy-2-butanone 4-phosphate synthase (EC 4.1.99.12) and/or GTP cyclohydrolase II (EC 3.5.4.25) also known as ribBA and/or 6,7-dimethyl-8-ribityllumazine synthase (EC 2.5.1.78) also known as ribH.

In a very specific embodiment, said strain of the present invention comprises an alteration at base 931,824 in the genome assembly NC_009513.1 of said type strain, in particular said alteration is a guanine to thymine alteration.

More specifically, the isolated *Limosilactobacillus* bacterial strain that shows alterations in one or more genes or regulatory sequences upstream of said genes that are associated with the riboflavin production pathway is the *Limosilactobacillus reuteri* (*L. reuteri*) species, said strain deposited at the BCCM under accession number LMG P-32020.

In a further aspect, the present application provides an isolated bacterial strain of the *Limosilactobacillus reuteri* (*L. reuteri*) species, said strain deposited at the BCCM under accession number LMG P-32020.

In accordance with an embodiment of the present application, the bacteria of the isolated bacterial strain are in suspension, freeze-dried, spray-dried, in live or inanimate/postbiotic form, or in prebiotic or synbiotic formulations, provided that active components are not disrupted.

In another further embodiment, the present application provides a composition comprising an isolated bacterial strain of the *L. reuteri* species deposited under accession number LMG P-32020. In a further embodiment, said composition comprises one or more pharmaceutically acceptable excipients, aromatizing agents or carriers. In an even further embodiment, said composition can optionally comprise other probiotic bacteria.

In accordance with an embodiment of the present application, the composition comprises an amount of bacteria in the range between $10^3$ to $10^{11}$ colony-forming units (CFU) for each gram of the composition.

The present application is based on the finding that the isolated bacterial strain *L. reuteri* AMBV339 shows a naturally occurring overproduction of riboflavin. Therefore, in an embodiment, the isolated bacterial strain or the composition of the present application is for use in the treatment and/or prevention of diseases associated with reduced levels of riboflavin in a subject. In a further aspect, said diseases associated with reduced levels of riboflavin are selected from the group comprising diseases of the nervous system, skin diseases, respiratory diseases, diseases associated with reduced levels of red blood cells, eye diseases, diseases associated with disturbed metabolism of iron, diseases associated with oxidative stress, general fatigue or general illness, urogenital diseases, metabolic diseases (e.g. associated with reduced vitamin levels), headache or migraine, pregnancy, gastrointestinal diseases, immune diseases, cancer and associated, viral, fungal and bacterial infections. More specifically, the isolated bacterial strain or the composition of the present invention is for use in the treatment and/or prevention of diseases associated with reduced riboflavin levels.

Alternatively, said strains or compositions of the invention are suitable for use in the prevention or treatment of gut microbiome dysbiosis, the promotion of gut microbiome resilience, and/or the promotion of health-associated gut taxa.

In another aspect, the non-therapeutic use of the isolated bacterial strain or the composition according to the present invention is disclosed for the prevention and/or reduction of general fatigue.

In still another aspect, the non-therapeutic use of the isolated bacterial strain or the composition according to the present invention is disclosed in cosmetics or personal care products.

In accordance with another embodiment, the use of the isolated bacterial strain or the composition according to the present invention in a process for the production of riboflavin is disclosed. In particular, said process for the production of riboflavin is a fermentation process.

In another aspect, the use of the isolated bacterial strain or the composition according to any of the embodiments of the invention as a probiotic or postbiotic, or in a prebiotic or synbiotic formulation, is disclosed. For example, It can be administered in oral or topical probiotic or postbiotic formulations.

In still another aspect, the use of the isolated bacterial strain or the composition according to any of the embodiments of the invention in the food or feed industry is disclosed.

In another aspect, the use of the isolated bacterial strain or the composition according to any of the embodiments of the invention as a colouring agent or as a starter culture in the food or feed industry is disclosed.

In accordance with another embodiment, the present application provides a process for the production of riboflavin. Said process is characterized in that the bacterial strain or the composition according to an embodiment of the present application, is incubated in an aqueous medium under conditions that allow that production of riboflavin.

In a further embodiment, said process for the production of riboflavin comprises the steps of: a) providing a bacterial strain or composition according to an embodiment of the present invention, b) incubating said bacterial strain or said composition in aqueous cultivation medium under conditions that allow the production of riboflavin; and optionally
c) isolating and purifying the riboflavin from the aqueous
cultivation medium.

BRIEF DESCRIPTION OF THE DRAWINGS

With specific reference now to the figures, it is stressed
that the particulars shown are by way of example and for
purposes of illustrative discussion of the different embodi-
ments of the present invention only. They are presented in
the cause of providing what is believed to be the most useful
and readily description of the principles and conceptual
aspects of the invention. In this regard no attempt is made to
show structural details of the invention in more detail than
is necessary for a fundamental understanding of the inven-
tion. The description taken with the drawings making appar-
ent to those skilled in the art how the several forms of the
invention may be embodied in practice.

FIG. 1: Regulatory intergenic region upstream of the
riboflavin operon of *L. reuteri* (ribD, ribE, ribBA and ribH
genes) with a guanine to thymine mutation in riboflavin-
overproducing *L. reuteri* AMBV339 compared to non-ribo-
flavin overproducing *L. reuteri* strains AMBV336,
AMBV337, AMBV368, AMBV369 and AMBV371, and the
type strain *L. reuteri* DSM20016.

FIG. 2: Estimation of production of riboflavin by *L.
reuteri* AMBV339.

Figure 4:
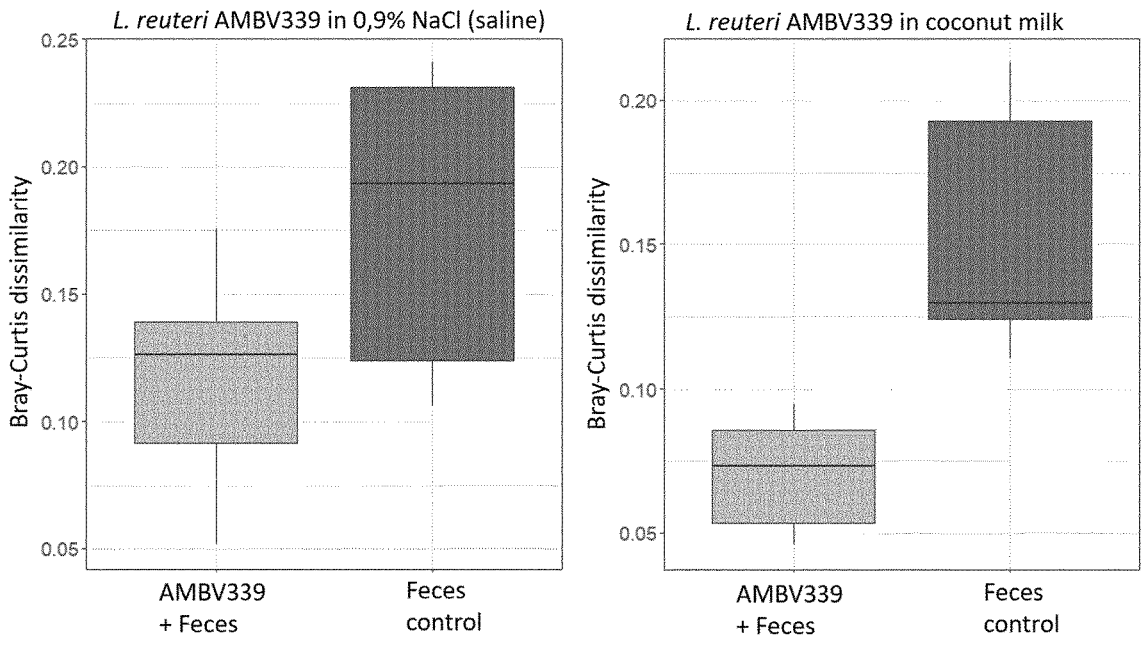

(A) Fluorescence characteristic of riboflavin quantified in
*L. reuteri* AMBV339 culture, cell-free culture supernatant
and cell pellet compared to a selection of other *L. reuteri*
strains and the commercial probiotic strains *Lacticaseiba-
cillus rhamnosus* GG and *L. reuteri* RC-14; p<0.05 indicates
statistically significant higher riboflavin fluorescence of the
AMBV339 condition compared to all other strains. (B & C)
Quantification of riboflavin concentrations in cultures of *L.
reuteri* AMBV339 and other vaginal *L. reuteri* AMBV336
and AMBV368, and the commercial probiotics *L. reuteri*
RC-14 and *L. rhamnosus* GG based on (A) fluorescence and
(B) absorbance of cultures plotted against a standard curve
of riboflavin dilutions. Measured values for the riboflavin
standard curve in MRS are depicted as grey circles with
corresponding riboflavin concentrations depicted on the
x-axis. Fluorescence and absorbance measurements of *L.
reuteri* AMBV339 (▲), AMBV336 (▼), AMBV368 (◆),
RC-14 (■) and *L. rhamnosus* GG ((◉)) are plotted within
the riboflavin standard curve.

FIG. 3. (A) Growth and (B) fluorescence characteristic of
riboflavin quantified in *L. reuteri* AMBV339 cultures in
food matrices compared to *L. reuteri* AMBV336 and *L.
reuteri* RC-14; (C) Fluorescence characteristic of riboflavin
quantified in *L. reuteri* AMBV339 co-cultured with starter
*Streptococcus thermophilus*. p<0.05 indicates statistically
significant higher riboflavin fluorescence of the AMBV336,
AMBV339 or RC-14 condition compared to the growth
medium condition.

FIG. 4. Longitudinal survival of *L. reuteri* AMBV339 in
(A) gastric juice at different pH, or (B) in different parts of
a simulated gastrointestinal tract inoculated with human
fecal microbiota; (C) Bray-Curtis dissimilarities between the
microbial community composition of the *L. reuteri*
AMBV339 in feces condition and feces as such (0.9% NaCl
and coconut milk). For the simulated gastrointestinal tract *L.
reuteri* AMBV339 in a 0.9% NaCl solution (or saline) or *L.
reuteri* AMBV339 culture in coconut milk was added. Data
is presented as means with standard deviation.

DETAILED DESCRIPTION OF THE INVENTION

The present invention will now be further described. In
the following passages, different aspects of the invention are
defined in more detail. Each aspect so defined may be
combined with any other aspect or aspects unless clearly
indicated to the contrary. In particular, any feature indicated
as being preferred or advantageous may be combined with
any other feature or features indicated as being preferred or
advantageous.

When describing the compounds of the invention, the
terms used are to be construed in accordance with the
following definitions, unless a context dictates otherwise.

As used in the specification and the appended claims, the
singular forms "a", "an", and "the" include plural referents
unless the context clearly dictates otherwise. By way of
example, "a compound" means one compound or more than
one compound.

The term "about" or "approximately" as used herein when
referring to a measurable value such as a parameter, an
amount, a temporal duration, and the like, is meant to
encompass variations of +/−10% or less, preferably +/−5%
or less, more preferably +/−1% or less, and still more
preferably +/−0.1% or less of and from the specified value,
insofar such variations are appropriate to perform in the
disclosed invention. It is to be understood that the value to
which the modifier "about" or "approximately" refers is
itself also specifically, and preferably, disclosed.

The present invention is based on the identification of a
novel *L. reuteri* strain, that was isolated from a healthy
human vaginal sample.

This strain is characterized by an alteration in one or more
genes or regulatory genetic sequences that are associated
with the riboflavin production pathway. Specific for the
novel isolated bacterial strain is that it exhibits natural
riboflavin-overproducing properties.

In the context of the present invention, the term alteration
is meant to be a modification of the genomic sequence
compared to the herein disclosed comparative strains such as
the other AMBV strains or the type strain. In particular, such
modification may constituted a mutation, deletion, insertion,
. . . in the genomic sequence of the strain.

In particular, the inventors identified that the *L. reuteri*
AMBV339 strain comprises riboflavin synthesis pathway
genes that are required for riboflavin production. More
specifically, growth of the *L. reuteri* AMBV339 strain in de
Man-Rogosa-Sharpe (MRS) medium or the tested food
matrices showed that the AMBV339 cultures exhibited a
yellow-green fluorescence characteristic for the presence of
riboflavin, which was not present in the other *L. reuteri*
strains that were tested. The riboflavin concentration in the
supernatant of the *L. reuteri* AMBV339 strain was quanti-
fied at approximately 18-40 μg riboflavin/ml using fluores-
cence-, absorbance- and HPLC/UV-based methods. Accord-
ing to the prior art related to riboflavin production by lactic
acid bacteria, these riboflavin concentrations are at least
3-20 times higher than the maximum riboflavin production
levels previously reported for other lactic acid bacteria
strains, depending on the detection method used.

Due to their fermenting and probiotic properties, lacto-
bacilli are often used in food/feed applications and supple-
ments. Indeed, also the *L. reuteri* AMBV339 strain has a
Qualified Presumption of Safety (QPS) status, indicating
that it can be directly used in feed, food and health applications. Furthermore, the AMBV339 strain also is efficiently growing and yielding high biomass overnight under the tested conditions.

The present application thus provides the isolated bacterial *L. reuteri* AMBV339 strain, typically characterized by a high level of riboflavin production. Further, also a composition comprising the *L. reuteri* AMBV339 strain is provided. The *L. reuteri* AMBV339 strain has been deposited with the Belgian Co-ordinated Collection of Micro-Organisms (BCCM) on Oct. 9, 2020 with the accession number LMG P-32020. The isolated AMBV339 strain or a composition comprising said strain is thus capable of producing riboflavin or vitamin B2 in high quantities.

In accordance with an embodiment of the present invention, the bacteria of the isolated bacterial AMBV339 strain can be provided in suspension, freeze-dried, spray-dried in live or postbiotic, prebiotic of synbiotic form, provided that the active components are not inactivated. In the context of the present invention, by means of the term "live form", "probiotic" and "synbiotic" form, reference is made to a form wherein the bacteria are alive. In the context of the present invention, by means of the term "postbiotic form" or "prebiotic form", reference is made to a form wherein the bacteria are not alive, such as in the case of inanimate applications or tyndalized versions of the bacteria or their molecular products.

In the context of the invention, the following definitions are used:

Probiotic=live microorganisms that, when administered in adequate amounts, confer a health benefit on the host Postbiotic=A preparation of inanimate microorganisms and/or their components that confers a health benefit on the host Prebiotics=a substrate that is selectively utilized by host microorganisms conferring a health benefit Synbiotic=a mixture comprising live microorganisms and substrate(s) selectively utilized by host microorganisms that confers a health benefit on the host Also a composition comprising the isolated bacterial stain AMBV339 is provided. The preparation of the compositions of the invention can be implemented by freeze-drying or spray-drying of bacterial cultures, mixing the dried bacteria both in suspension with water or with further suitable excipients and optionally with addition of further active principles.

As used herein, a "composition", refers to any mixture of two or more products or compounds (e.g. agents, modulators, regulators, etc.). It can be a solution, a suspension, liquid, powder or a paste, aqueous or non-aqueous formulations or any combination thereof. In the context of the present invention, the compositions are preferably pharmaceutical or cosmetic compositions, comprising one or more pharmaceutically excipients, or diluents, such as suitable sugars, copolymers PEG/PPG, or cryoprotectants.

In one embodiment, said composition comprises one or more pharmaceutically acceptable excipients, aromatizing agents or carriers. Examples of excipients that can be selected in such compositions are rubber, xanthan, carboxymethyl cellulose, silicone, Vaseline, white soft paraffin, magnesium stearate, maltodextrin, mannitol, starch, glucose, trehalose, glycerine, propylene glycol, lactose, and similar.

The compositions may also comprise aromatizing agents; such as thyme or any extract thereof. In accordance with an embodiment of the present invention, the carriers provide an improvement of the bioavailability, the stability and/or the endurance of the microorganism.

The compositions may thus further comprise one or more carriers in order to improve the bioavailability, the stability and the endurance of the microorganism. The carrier may also improve the adhesion of the bacterial strain to a suitable surface, for example the mucosal surface. Such a carrier can for example by exopolysaccharides produced by *S. salivarius* or lactobacilli. Further, the carrier may be a heat-sensitive polymer able to increase the viscosity and thus the adhesiveness by increasing the temperature or Gantrex for example. In another embodiment, the carrier can be hydroxypropyl methylcellulose (HPMC).

In accordance with an embodiment of the present invention, the composition comprises an amount of bacteria that is preferably in the range between $10^3$ to $10^{11}$ CFU for each gram of the composition.

In a further aspect, the present invention relates to the isolated bacterial strain AMBV339 or the composition comprising said strain according to the invention for use as a medicament in human or veterinary medicine. In particular, the isolated bacterial strain or the composition according to the invention is for use in the treatment and/or prevention of diseases associated with reduced levels of riboflavin in a subject. In another embodiment, the isolated bacterial strain or the composition of the present invention is for use in the treatment and/or prevention of diseases for which a boost of riboflavin is desirable in a subject. In a further aspect, the diseases associated with reduced levels of riboflavin are selected from the group comprising diseases of the nervous system, skin diseases, respiratory diseases, diseases associated with reduced levels of red blood cells, eye diseases, diseases associated with disturbed metabolism of iron, diseases associated with oxidative stress, general fatigue or general illness, urogenital diseases, metabolic diseases (e.g. associated with reduced vitamin levels), headache or migraine, pregnancy, gastrointestinal diseases, immune diseases, cancer and associated, viral, fungal and bacterial infections. More specifically, the isolated bacterial strain or the composition of the present invention is for use in the treatment and/or prevention of diseases associated with reduced riboflavin levels.

In another aspect, the present invention relates to a method of treatment of a disease in a subject by administration of the isolated bacterial strain AMBV339 or the composition comprising said strain to a subject. In particular, the disease can be selected from diseases for which a boost of riboflavin is desirable. In a further aspect, said diseases associated with reduced levels of riboflavin are selected from the group comprising diseases of the nervous system, skin diseases, respiratory diseases, diseases associated with reduced levels of red blood cells, eye diseases, diseases associated with disturbed metabolism of iron, diseases associated with oxidative stress, general fatigue or general illness, urogenital diseases, metabolic diseases (e.g. associated with reduced vitamin levels), headache or migraine, pregnancy, gastrointestinal diseases, immune diseases, cancer and associated, viral, fungal and bacterial infections. More specifically, the invention is related to a method of treatment of a disease associated with reduced riboflavin levels in a subject by the administration of the isolated bacterial strain AMBV339 or the composition comprising said strain to the subject.

The terms "treatment", "treating", "treat" and the like refer to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" covers any treatment of a disease in a mammal, in particular a human, and includes: (a) preventing the disease or symptom from occurring in a subject which may be predisposed to the disease or symptom but has not yet been diagnosed as having it; (b) inhibiting the disease symptoms, i.e. arresting its development; or (c) relieving the disease symptoms, i.e. causing regression of the disease or symptom. In the context of the present invention, the terms "prevention" and the like refer to preventing a disease or conditions from happening. In the context of the present invention, the term "immuno-modulation" refers to the process of altering an immune response to a desired level and/or direction.

In a further aspect, the isolated bacterial strain or composition of the present invention can be used in the non-therapeutic reduction and/or prevention of general fatigue. Thus, the present application also provides the non-therapeutic use of the isolated bacterial strain or composition of the invention for the prevention and/or reduction of general fatigue or weakness. The term "non-therapeutic" and the like refers to obtaining a desired physiological effect in a non-disease context, and thus before any signs of a disease are present in the subject. In another aspect, the use of the isolated bacterial strain or composition of the present invention is disclosed as a supplemental intake of riboflavin.

In another aspect, the non-therapeutic use of the isolated bacterial strain or composition of the present invention in cosmetics or personal care products is disclosed. In a specific embodiment, the non-therapeutic use of the isolated bacterial strain or composition of the present invention in cosmetics is disclosed. The form of the cosmetics of the present invention is not particularly limited, and it is possible to provide the cosmetics as emulsion, liquid, cream, solid, or paste. The cosmetics can also be provided as agent, gel, powder, mousse or spray. For example, the cosmetics can be selected from skin cosmetics, makeup or hairdressing cosmetics. Skin cosmetics can include cleaning products, anti-transpiration products, hydration products, UV resistance products, etc. Hair-dressing cosmetics can include hair cleaning products, such as shampoo, hair coloring products, products for improving hair-growing, hair rinse products or hair conditioning products. The cosmetic products can also include cleansing gels, cleansing cream, cleaning foam, cleaning lotion, liquid soaps, hand soaps, bath oil, saving cream. Makeup cosmetics may include foundation powder, face powder, lipstick, lip gloss, eyeliner, eye cream, mascara, rouge, manicure oil and other products, nail polish.

In a specific embodiment, the non-therapeutic use of the isolated bacterial strain or composition of the present invention in personal care products is disclosed. Said personal care products may include but are not limited to personal hygiene and cleansing products, oral care products such as tooth paste, eye care products, ear care products, sanitary products.

One aspect of the present application discloses the use of the isolated bacterial strain or composition according to the invention as a probiotic or postbiotic. Probiotics are defined as live microorganisms that exert beneficial effects on the host when administered in adequate amounts. In the context of the present invention, for postbiotics is intended any factor resulting from the metabolic activity of a probiotic or any released molecule capable of conferring beneficial effects to the host in a direct or indirect way. The term "postbiotic", "fermented product" or "fermented supernatant" in the context of the present invention may thus comprise also any factor resulting from the metabolic activity of the isolated bacterial strain of the present invention, capable of conferring beneficial effects to the host in a direct or indirect way.

In a further aspect, the use of the isolated bacterial strain or composition according to the invention in the food or feed industry is provided; in particular in the production of dairy and non-dairy fermentation products, dietary supplements, dietary food additives and/or nutraceuticals. Said food industry can thus encompass fermented food products (dairy-based worth, soy). Said food industry can also include the bioreactors and processing environments used in the production of food products, wherein the bacterial strain or the composition of the present invention can be added to the food products during production.

In a specific embodiment, the non-therapeutic use of the isolated bacterial strain or composition of the present invention in food supplementation is thus disclosed. The isolated bacterial strain or composition can thus be provided as a food supplement, alternatively it may suitably be used as a colouring agent in the food or feed industry.

In still another aspect, the use of the isolated bacterial strain or the composition of the present invention is disclosed in a process for the production of riboflavin. Since the isolated bacterial strain of the present invention is characterized for its high levels of naturally occurring riboflavin production, it is highly suitable for the production of riboflavin.

In a further embodiment, the present application also discloses a process for the production of riboflavin. In said process the bacterial strain or the composition according to any of the disclosed embodiments is incubated in aqueous medium under conditions that allow the production of riboflavin from a given substrate. The aqueous medium is typically an aqueous medium comprising for instance salts, substrate(s), and a certain pH. The medium is also referred to as production medium.

The process may thus comprise the steps of: (a) providing a bacterial strain or a composition according to any of the disclosed embodiments, (b) incubating said bacterial strain or said composition in aqueous cultivation medium under conditions that allow the production of riboflavin; and optionally (c) isolating and purifying the riboflavin from the aqueous cultivation medium.

"Fermentation" or "production" or "fermentation process" as used herein may be the use of growing bacterial cells using media, conditions and procedures known to the skilled person.

The produced riboflavin may be recovered from the cells by any suitable means. Recovering means for instance that the produced riboflavin may be separated from the production medium. Optionally, the thus produced fermentation product may be further processed, e.g. purified.

In connection with the process according to the present invention, the growing step of the bacteria can be performed in an aqueous medium, i.e. the growth medium, supplemented with appropriate nutrients for growth normally under aerobic conditions. The cultivation may be conducted, for instance, in batch, fed-batch, semi-continuous, or continuous mode.

The terms "production" or "productivity" are art-recognized and include the concentration of riboflavin formed with a given time and a given fermentation volume (e.g. kg product per hour per liter). The term "efficiency of production" includes the time required for a particular level of production to be achieved. The term "yield" is art-recognized and includes the efficiency of the production of riboflavin.

The isolated bacterial strain or the composition according to the present invention can be in any form suitable to be administered topically, orally, or through the respiratory tract. Further, the bacterial strain or composition according to the present invention can be in a pharmaceutical form selected from, but not limited to, a spray, cream, lotion, gel, an ointment, a solution, a suspension, an emulsion, a capsule, a tablet, a powder, a granule, drops, inhaler, tooth paste, mouth wash. The bacterial strain or composition can further be formulated in such a manner that it can be administered through the respiratory tract by a nebulizer, with or without propellants. Finally, and in a preferred embodiment, the bacterial strain or composition can also be formulated in such a manner that it can be administered via vaginal administration. For example, the bacterial strain or composition of the present invention can be provided as a vaginal wash solution, vaginal soap, vaginal cream, tampon or vaginal pill.

As used herein, the term "subject" refers to any living organisms. The subject can thus be a mammal, a fish or a bird. Preferably, it refers to a human subject or a non-human mammal. Even more preferably, the subject is a human subject. In another particular embodiment, the subject is a production or farm animal, or a pet. The production or farm animal can be selected from the group comprising a pig, sheep, a goat, a cow, a horse, a chicken, a goose, a turkey, or a rabbit. The pet can be selected from a cat or a dog.

Examples

Materials and Methods

Whole-Genome Sequencing of the *L. reuteri* AMBV339Strain and Gene Annotation

The strain was grown overnight in de Man-Rogosa-Sharpe (MRS) medium (Carl Roth, Karlsruhe, Germany). In duplicate, 1.5 ml culture was transferred to a sterile tube and ampicillin was added at 100 μg/ml. After 1 h of incubation at 37° C., the culture was centrifuged for 3 min at 12.000 g. The resulting cell pellets were washed three times with sterile NaCl-EDTA (0.8766 g NaCl and 0.292 g EDTA in 0.5 L distilled water) and resuspended in 100 μl NaCl-EDTA. Then, 100 μl of lysozyme (10 mg/ml) and 1 μl of RNase (20 mg/ml) were added for 1 h at 37° C. Next, 229 μl NaCl-EDTA, 50 μl 10% SDS and 20 μl Proteinase K (20 mg/ml) were added, vortexed and incubated for 1 h at 55° C. After incubation, 200 μl of a cold protein precipitation solution (6 ml of 5M CH3COOK, 1.15 ml Glacial acetic acid and 2.85 ml distilled water) was added and vortexed at maximum speed for 20 sec and incubated on ice for 5 min. Then, the solution was centrifuged for 3 min at 4° C. and 12.000 g. The supernatant was transferred to a clean 1.5 ml tube and centrifuged for 3 min at 4° C. and 12.000 g. The resulting supernatant was transferred to a clean 1.5 ml tube and DNA was precipitated with 600 μl of ice-cold isopropanol. After a centrifugation step of 3 min at 4° C. and 12.000 g the supernatant was discarded and the pellet was resuspended with 600 μl fresh 70% EtOH. After a centrifugation step of 3 min at 4° C. and 12.000 g the supernatant was discarded and the pellet was left to air-dry until all the ethanol evaporated. The DNA pellet was dissolved in 50 μl distilled water and incubated for 5 min at 55° C.

Whole-genome sequencing was performed using the Nextera XT DNA Sample Preparation kit (Illumina, San Diego, CA, USA) and the Illumina MiSeq platform, using 2×250 cycles, at the Laboratory of Medical Microbiology (University of Antwerp, Antwerp, Belgium). Gene annotation was performed using the Pathosystems Resource Integration Center (PATRIC) and presence of riboflavin genes was determined based on the Kyoto Encyclopedia of Genes and Genomes (KEGG) Pathways.

Riboflavin Quantification Based on Fluorescence

Quantitative analysis of riboflavin production in culture medium based on fluorescence was performed according to a modified method previously described. Lactobacilli were either inoculated in MRS broth as growth medium (Difco) and incubated statically overnight at 37° C., or inoculated in commercially obtained food matrices (coconut milk, soy milk, whole and semi-skimmed cow milk, butter milk, apple juice or MRS broth as control) and incubated statically for 96 h at 37° C.

To obtain cell-free culture supernatant, the bacterial culture in MRS was subsequently centrifuged (2486 g, 10 min) and the supernatant was filter sterilized (through a 0.2 μm filter) to obtain cell-free culture supernatant. The resulting cell pellet was washed twice in phosphate-buffered saline (PBS) and resuspended in fresh MRS. For fluorescence measurements, the fluorescence of 100 μl of the whole cell culture, cell-free supernatant or cell pellet was measured in a 96-well plate using the Synergy HTX Multi-mode microplate reader (BioTek) with the 485/20 excitation filter and 520/20 emission filter. Serial dilutions of riboflavin powder in MRS obtained commercially were used to obtain a standard curve as reference for quantification. Statistical analysis was performed with a two-way ANOVA.

Riboflavin Quantification Based on Absorbance

Quantitative analysis of riboflavin production in culture medium based on absorbance at 444 nm was performed according to Sauer et al. (1996). Lactobacilli were inoculated in MRS medium and incubated statically overnight at 37° C. The culture was subsequently centrifuged (2486 g, 10 min) and the supernatant was filter sterilized (through a 0.2 μm filter) to obtain cell-free culture supernatant. Then, 0.2 ml of 1 M NaOH were added to 0.8 ml of cell-free culture supernatant, and 0.4 ml of the resulting solution was neutralized with 1 ml of 0.1 M potassium phosphate buffer (pH 6.0). The absorbance at 444 nm was measured in a 96-well plate using the Synergy HTX Multi-mode microplate reader (BioTek). Serial dilutions of riboflavin powder in MRS obtained commercially were used to obtain a standard curve as reference for quantification. Statistical analysis was performed with a two-way ANOVA.

Riboflavin Quantification with HPLC-UV

Riboflavin concentration was measured in cell-free culture supernatant samples with a standard isocratic method for HPLC-UV based on that from the European Pharmacopoeia methodology for vitamin B12. Lactobacilli were either inoculated in MRS broth as growth medium (Difco) and incubated statically overnight at 37° C., or inoculated in commercially obtained food matrices (coconut milk, butter milk or MRS broth as control) and incubated statically for 96 h at 37° C. To obtain cell-free culture supernatant, the bacterial culture was subsequently centrifuged (2486 g, min) and the supernatant was collected. For HPLC-UV measurements, samples were diluted with both medium and mobile phase from the HPLC, and tested in duplicate with 2 standard series. Samples and control were also spiked with riboflavin.

Quantification of Bacterial Growth

Bacterial growth in food matrices was quantified by preparing serial tenfold dilutions of bacterial cultures in sterile PBS and plating them out on MRS agar. The plates were incubated at 37° C. for 1-2 days and colonies corresponding to each serial dilution were subsequently counted. Bacterial growth was expressed as colony-forming units (CFU)/ml culture.

Survival and Microbiome Modulation Testing of *L. reuteri* AMBV339 in a Simulated Gastrointestinal Tract System Live *L. reuteri* AMBV339 washed and resuspended in saline (0.9% NaCl) at ~1.5×10^9 CFU/ml or *L. reuteri* AMBV339 cultured in coconut milk were added to a simulated human gastrointestinal system set-up cfr. Mortelé et al. (2019). Briefly, the system consisted of vessels representing the stomach (37° C., volume: 34 ml, pH 2-4, reagents added: 16 ml), small intestine (37° C., volume: 50 ml, pH 7.5, reagents added: 15 ml) and different parts of the large intestine (37° C., anaerobic, volume: 65 ml, pH: 5.8, reagents added: 55 ml). The small and large intestine parts were inoculated with human fecal microbiota. Samples were taken from the system at regular time points to assess *L. reuteri* AMBV339 survival via plating out on MRS agar, and to analyze the fecal microbiome composition using 16S rRNA sequencing with subsequent bioinformatics analysis in R studio.

Results

Genes of the Riboflavin Production Pathway are Present in *Limosilactobacillus reuteri* AMBV339

The whole genome of the *L. reuteri* AMBV339 strain has been sequenced and annotated. All genes of the riboflavin synthesis pathway required for riboflavin production and possibly transport have been detected in the genome of *L. reuteri* AMBV339, including those for:

3,4-dihydroxy-2-butanone 4-phosphate synthase (EC 4.1.99.12)/GTP cyclohydrolase II (EC 3.5.4.25)

Diaminohydroxyphosphoribosylaminopyrimidine deaminase (EC 3.5.4.26)/5-amino-6-(5-phosphoribosylamino)uracil reductase (EC 1.1.1.193)

6,7-dimethyl-8-ribityllumazine synthase (EC 2.5.1.78)

Riboflavin synthase eubacterial/eukaryotic (EC 2.5.1.9)

FMN adenylyltransferase (EC 2.7.7.2)/Riboflavin kinase (EC 2.7.1.26)

RibT protein, riboflavin biosynthesis acetyltransferase (GNAT) family

Substrate-specific component RibU of riboflavin ECF transporter

A naturally present genetic alteration compared to several other non-riboflavin-overproducing *L. reuteri* isolates such as *L. reuteri* AMBV336 and *L. reuteri* AMBV337, as well as the type strain *L. reuteri* DSM20016, has been detected in *L. reuteri* AMBV339 using a bioinformatics-based alignment of the strain genomes. The genetic alteration was found to be specifically in the regulatory region upstream of the gene cluster responsible for riboflavin synthesis comprising the sequences for Diaminohydroxyphosphoribosylaminopyrimidine deaminase (EC 3.5.4.26)/5-amino-6-(5-phosphoribosylamino) uracil reductase (EC 1.1.1.193), Riboflavin synthase eubacterial/eukaryotic (EC 2.5.1.9), 3,4-dihydroxy-2-butanone 4-phosphate synthase (EC 4.1.99.12)/ GTP cyclohydrolase II (EC 3.5.4.25) and/or 6,7-dimethyl-8-ribityllumazine synthase (EC 2.5.1.78) as depicted in FIG. 1. In the genome assembly NC_009513.1 of the strain *L. reuteri* DSM20016 (type strain of the species; https://lpsn.dsmz.de/species/*limosilactobacillus-reuteri*), the location of this genetic alteration is at base 931,824 (guanine in *L. reuteri* DSM20016 to thymine in *L. reuteri* AMBV339).

Riboflavin is Produced by *L. reuteri* AMBV339 in High Concentrations in Laboratory Medium High levels of fluorescence characteristic of riboflavin (excitation at approx. 440 nm and emission at approx. 520 nm) were observed in *L. reuteri* AMBV339 whole culture grown overnight in MRS and the corresponding cell-free culture supernatant (FIG. 2A). The fluorescence was much lower in the cell pellet, suggesting that riboflavin is mostly excreted. Compared to *L. reuteri* AMBV339, the fluorescence detected in whole cultures, cell-free culture supernatants and cell pellets of a selection of other vaginal *L. reuteri* strains AMBV336, AMBV337, AMBV368, AMBV369 and AMBV371 isolated from the same participant, and the commercial probiotic strains *L. reuteri* RC-14 and *Lacticaseibacillus rhamnosus* GG was negligible, indicating low levels or no riboflavin production.

Initial quantification of riboflavin production in *L. reuteri* AMBV339 supernatant was performed against a standard curve based on serial dilutions of pure riboflavin in MRS. Two complementary methods were implemented: fluorescence-based detection of riboflavin in solution with excitation at approx. 440 nm and emission at 520 nm and quantitative analysis of riboflavin in solution using absorbance at 444 nm. With both methods, riboflavin in *L. reuteri* AMBV339 supernatant was quantified at approximately 40 μg/ml, while the riboflavin levels in culture supernatants of other vaginal *L. reuteri* AMBV336 and AMBV368, and the commercial probiotics *L. reuteri* RC-14 and *L. rhamnosus* GG, were close to zero (FIGS. 2B & C).

These results were validated using standard HPLC-UV for vitamin detection, which quantified riboflavin in the supernatant of overnight *L. reuteri* AMBV339 culture in MRS at approximately 18.7 μg/ml. No riboflavin was detected in culture supernatants of *L. rhamnosus* GG, while the other *L. reuteri* tested had the following riboflavin concentrations in their overnight culture supernatant: *L. reuteri* AMBV336 0.933 μg/ml, *L. reuteri* AMBV337 0.604 μg/ml, *L. reuteri* L. reuteri AMBV368 0.953 μg/ml, *L. reuteri* AMBV369 0.706 μg/ml, *L. reuteri* AMBV370 0.953 μg/ml, *L. reuteri* AMBV371 0.585 μg/ml and *L. reuteri* RC-14 0.423 μg/ml.

*L. reuteri* AMBV339 Grows and Produces Riboflavin in Various Milk Food Matrices Growth (FIG. 3A) and fluorescence as read-out for riboflavin production (FIG. 3B) of *L. reuteri* AMBV339 was assessed in a number of commercially available food matrices: coconut milk, soy milk, whole and semi-skimmed cow milk, butter milk, apple juice or MRS broth as control, and compared to *L. reuteri* AMBV336 and *L. reuteri* RC-14.

All *L. reuteri* strains grew well in coconut milk, soy milk, whole and semi-skimmed cow milk, butter milk and MRS, and their growth was negligible in apple juice (FIG. 3A). *L. reuteri* AMBV339 reached the highest colony-forming units (CFU)/ml in coconut milk (6.07E+10 CFU/ml), soy milk (5.00E+10 CFU/ml), and whole cow milk (4.20E+10 CFU/ml), followed by butter milk (1.50E+08 CFU/ml), MRS (6.70E+08 CFU/ml) and semi-skimmed milk (1.07E+07 CFU/ml). Thus, growth of *L. reuteri* AMBV339 in food matrices was similar to the growth of the commercial probiotic strain *L. reuteri* RC-14, especially in coconut milk, soy milk and whole cow milk.

High levels of fluorescence reflective of riboflavin production were detected in *L. reuteri* AMBV339 cultures in all food matrices (coconut milk, soy milk, whole and semi-skimmed cow milk, butter milk), except for apple juice, which is likely due to lack of growth in apple juice. The fluorescence of *L. reuteri* AMBV336 and *L. reuteri* RC-14 in the same food matrices was significantly lower, indicating low levels or no riboflavin production.

Highest riboflavin production by *L. reuteri* AMBV339 relative to the baseline was detected in coconut milk (FIG. 3B). The corresponding fluorescence values were similar to those in MRS, therefore riboflavin production by *L. reuteri* AMBV339 in coconut milk is expected to lie in the range of 18-40 µg/ml. Highest absolute fluorescence was detected in *L. reuteri* AMBV339 cultures in butter milk.

Also when *L. reuteri* AMBV339 was co-cultured in coconut milk with the widely used dairy starter *Streptococcus thermophilus*, it retained its high fluorescence values indicative of riboflavin production (FIG. 3C). Consequently, it is possible to use *L. reuteri* AMBV339 not only as such, but also in combination with other starter cultures for riboflavin production in fermented foods. *L. reuteri* AMBV339 cells resuspended in a 0.9% NaCl solution or *L. reuteri* AMBV339 culture in coconut milk were also inoculated into a simulated human gastrointestinal tract. *L. reuteri* AMBV339 survived throughout the simulated human gastrointestinal tract (FIG. 4A). Specifically, it survived the conditions of gastric juice at pH 2, 3 and 4 for 90 minutes, as shown in FIG. 4A, resulting in $10^6$-$10^{11}$ CFU/ml. This indicates that *L. reuteri* AMBV339 can survive the three different acidic conditions of the stomach up to 90 minutes. Also in the small and large intestine, an average of $10^5$ CFU/ml *L. reuteri* AMBV339 survived when delivered in coconut milk after 72 hours in the simulated gastrointestinal tract and an average of $10^5$ CFU/ml survived when delivered in a 0.9% NaCl solution (FIG. 4B).

Consistent modulation of the fecal microbiome composition was observed due to the addition of *L. reuteri* AMBV339 to the simulated gastrointestinal tract, reflected in increased dissimilarity of the microbiome of feces with added *L. reuteri* AMBV339 compared to feces as such (FIG. 4C). This microbiome modulating effect of *L. reuteri* AMBV339 could have potential beneficial properties on species that can profit from the addition of a riboflavin-overproducing strain such as *L. reuteri* AMBV339.

To conclude, high production of riboflavin by the healthy human isolate *L. reuteri* AMBV339 was demonstrated in laboratory conditions and in food matrices. The genome sequence of *L. reuteri* AMBV339 was shown to contain all genes of the riboflavin synthesis pathway with a mutation in the regulatory genetic sequence, suggesting its natural ability to overproduce riboflavin. Fluorescence-, absorbance- and HPLC-UV-based measurements against riboflavin standard curves quantified natural riboflavin production in *L. reuteri* AMBV339 cultures and cell-free supernatant at approximately 18-40 µg/ml, while riboflavin levels in cultures of all other tested *L. reuteri* strains and *L. rhamnosus* GG were close to zero. Riboflavin production levels by *L. reuteri* AMBV339 are thus significantly higher than those reported for natural production by other lactobacilli in literature (2.3-3 µg/ml). Furthermore, *L. reuteri* AMBV339 grew well in a range of food matrices (coconut milk, soy milk, whole and semi-skimmed cow milk, butter milk) at levels comparable to the commercial probiotic *L. reuteri* RC-14. In all of these food matrices, significant riboflavin production by *L. reuteri* AMBV339 was detected, with highest riboflavin production relative to baseline estimated in coconut milk in the range of 18-40 µg/ml, and highest absolute levels of riboflavin reached in butter milk. Finally, *L. reuteri* AMBV339 survived in simulated conditions of the human gastrointestinal tract and provided fecal microbiome modulation.

REFERENCES

Dey, S., Bishayi, B. (2016). Riboflavin along with antibiotics balances reactive oxygen species and inflammatory cytokines and controls *Staphylococcus aureus* infection by boosting murine macrophage function and regulates inflammation. J Inflamm (Lond). 13:36. doi:10.1186/s12950-016-0145-0.

Jayashree, S., Jayaraman, K., and Kalaichelvan, G. (2010) Isolation, screening and characterization of riboflavin producing lactic acid bacteria from Katpadi, Vellore district. Recent Res Sci Technol 2: 83-88.

Juarez del Valle, M., Laiño, J. E., Savoy de Giori, G., & LeBlanc, J. G. (2017). Factors stimulating riboflavin produced by *Lactobacillus plantarum* CRL 725 grown in a semi-defined medium. Journal of Basic Microbiology, 57(3), 245-252.

Lim, S. H., Choi, J. S., & Park, E. Y. (2001). Microbial production of riboflavin using riboflavin overproducers, *Ashbya gossypii, Bacillus subtilis*, and *Candida famate*: An overview. Biotechnology and Bioprocess Engineering, 6(2), 75-88.

Mortelé, O., Iturrospe, E., Breynaert, A., Verdickt, E., Xavier, B. B., Lammens, C., Malhotra-Kumar, S., Jorens, P. G., Pieters, L., van Nuijs, A., & Hermans, N. (2019). Optimization of an in vitro gut microbiome biotransformation platform with chlorogenic acid as model compound: From fecal sample to biotransformation product identification. Journal of pharmaceutical and biomedical analysis, 175, 112768.

Stahmann, K. P., Revuelta, J. L., & Seulberger, H. (2000). Three biotechnical processes using *Ashbya gossypii, Candida famata*, or *Bacillus subtilis* compete with chemical riboflavin production. Applied Microbiology and Biotechnology, 53(5), 509-516.

Thakur, K., Tomar, S. K., & De, S. (2016). Lactic acid bacteria as a cell factory for riboflavin production. Microbial Biotechnology, 9(4), 441-451.

Thakur, K., and Tomar, S. K. (2015) Exploring indigenous *Lactobacillus* species from diverse niches for riboflavin production. J Young Pharmacists 7: 122-127.

The invention claimed is:

1. A method of supplementing a subject experiencing riboflavin deficiency, the method comprising administering a probiotic or synbiotic composition to the subject, the probiotic or synbiotic composition comprising an isolated bacterial strain of *Lactobacillus reuteri*, the strain deposited under accession number LMG P-32020.

2. The method according to claim 1, wherein the probiotic or synbiotic composition further comprises one or more additional strains of probiotic bacteria.

3. The method according to claim 2, wherein the one or more additional strains of probiotic bacteria comprises *Streptococcus thermophilus*.

4. The method according to claim 1, wherein the probiotic or synbiotic composition further comprises one or more food matrices selected from the group consisting of coconut milk, soy milk, cow's milk, and buttermilk.

5. The method according to claim 4, wherein the food matrix is coconut milk.

6. The method according to claim 1, wherein the probiotic or synbiotic composition further comprises an animal feed.

7. The method according to claim 1, wherein the probiotic or synbiotic composition further comprises a food coloring.

8. The method according to claim 7, wherein the food coloring is E101.

9. The method according to claim 1, wherein the subject experiencing riboflavin deficiency is suffering from a disease selected from the group consisting of diseases of the nervous system, skin diseases, respiratory diseases, diseases associated with reduced levels of red blood cells, eye diseases, diseases associated with disturbed metabolism of iron, diseases associated with oxidative stress, urogenital diseases or infections, gastrointestinal diseases, general fatigue or weakness, metabolic diseases, immune diseases, headache or migraine, cancer, viral, bacterial, and fungal infections.

10. The method according to claim 1, wherein the subject experiencing riboflavin deficiency is a pregnant or lactating human.

11. The method according to claim 1, wherein the subject experiencing riboflavin deficiency is experiencing general fatigue or weakness.

12. The method according to claim 1, wherein the subject experiencing riboflavin deficiency is experiencing one or more symptoms selected from the group consisting of skin damage, sore throat, edema of oral and mucous membranes, cheilosis, and glossitis.

13. The method according to claim 1, wherein the subject experiencing riboflavin deficiency is a non-human mammal.

14. The method according to claim 13, wherein the non-human mammal is selected from the group consisting of pigs, sheep, goats, cows, horses, chickens, geese, turkeys, rabbits, cats, and dogs.

15. The method according to claim 1, wherein the *Lactobacillus reuteri* produces riboflavin in the probiotic composition.

16. The method according to claim 15, wherein the probiotic composition is a solution, suspension, liquid, or paste, and the riboflavin produced by the *Lactobacillus reuteri* is present in a concentration of from about 18 µg/ml to about 40 µg/mL.

* * * * *